(12) United States Patent
Biel

(10) Patent No.: US 7,070,611 B2
(45) Date of Patent: Jul. 4, 2006

(54) TREATMENT DEVICE FOR TOPICAL PHOTODYNAMIC THERAPY AND METHOD OF USING SAME

(75) Inventor: Merrill A. Biel, Mendota Heights, MN (US)

(73) Assignee: Advanced Photodynamic Technologies, Inc., Minneapolis, MN (US)

( * ) Notice: Subject to any disclaimer, the term of this patent is extended or adjusted under 35 U.S.C. 154(b) by 12 days.

(21) Appl. No.: 10/208,632

(22) Filed: Jul. 29, 2002

(65) Prior Publication Data

US 2003/0009205 A1    Jan. 9, 2003

Related U.S. Application Data

(63) Continuation-in-part of application No. 09/513,036, filed on Feb. 25, 2000, now abandoned.

(51) Int. Cl.
*A61N 5/06* (2006.01)

(52) U.S. Cl. .......................... 607/88; 128/872
(58) Field of Classification Search ............... 604/20; 606/4–6, 88–90, 94, 14; 607/88–92; 128/898, 128/872
See application file for complete search history.

(56) References Cited

U.S. PATENT DOCUMENTS

| 4,185,633 A | 1/1980 | Prozorov et al. ......... 128/303.1 |
| 4,234,907 A | 11/1980 | Daniel ......................... 362/32 |
| 4,502,487 A | 3/1985 | DuBrucq et al. ........... 128/665 |
| 4,646,743 A | 3/1987 | Parris ........................ 128/396 |
| 4,686,986 A * | 8/1987 | Fenyo et al. .................. 607/90 |
| 4,736,745 A | 4/1988 | Gluckman |
| 4,761,047 A | 8/1988 | Mori ......................... 350/96.1 |
| 4,791,926 A | 12/1988 | Fry ........................... 128/303.1 |
| 4,852,549 A | 8/1989 | Mori ........................... 128/395 |
| 5,104,392 A | 4/1992 | Kittrell et al. ................. 606/15 |
| 5,109,859 A | 5/1992 | Jenkins .................. 128/662.03 |
| 5,259,380 A | 11/1993 | Mendes et al. |
| 5,358,503 A | 10/1994 | Bertwell et al. .............. 606/27 |
| 5,445,608 A * | 8/1995 | Chen et al. .................. 604/20 |
| 5,500,009 A | 3/1996 | Mendes et al. |
| 5,505,726 A | 4/1996 | Meserol |
| 5,616,140 A | 4/1997 | Prescott ....................... 606/10 |
| 5,634,711 A * | 6/1997 | Kennedy et al. ............ 362/119 |
| 5,683,436 A | 11/1997 | Mendes et al. |
| 5,698,866 A | 12/1997 | Doiron et al. |
| 5,782,896 A * | 7/1998 | Chen et al. .................... 607/88 |
| 5,797,868 A | 8/1998 | Leone |
| 5,800,478 A | 9/1998 | Chen et al. |

(Continued)

FOREIGN PATENT DOCUMENTS

JP      07240536     12/1995

(Continued)

*Primary Examiner*—Michael Peffley
*Assistant Examiner*—Pete Vrettakos
(74) *Attorney, Agent, or Firm*—Fulbright & Jaworski L.L.P.

(57) ABSTRACT

The invention relates to a light emitting treatment device including one or more light members which are configured to emit energy for photodynamic therapy at a treatment field. The treatment device may be made of a polymeric material configured to conform to a body surface. The light members may be disposed in a substantially uniform array and be configured to emit energy in a substantially uniform pattern. The light emitting treatment device may provide light variable feedback to a control apparatus. The light emitting treatment device may further include a heat dissipating layer, a layer of gold or gold alloy, or a layer of adhesive disposed on at least one of the one or more surfaces. Methods of using the treatment device are also disclosed.

16 Claims, 6 Drawing Sheets

U.S. PATENT DOCUMENTS

| | | | |
|---|---|---|---|
| 5,814,041 A | 9/1998 | Anderson et al. | |
| 6,048,359 A | 4/2000 | Biel | 607/92 |
| 6,063,108 A | 5/2000 | Salansky et al. | |
| 6,086,558 A * | 7/2000 | Bower et al. | 604/96.01 |
| 6,159,236 A * | 12/2000 | Biel | 607/92 |
| 6,251,127 B1 * | 6/2001 | Biel | 607/88 |
| 6,290,713 B1 | 9/2001 | Russell | |
| 6,602,274 B1 | 8/2003 | Chen | |
| 6,622,049 B1 * | 9/2003 | Penner et al. | 607/88 |
| 6,623,513 B1 * | 9/2003 | Biel | 607/88 |
| 2002/0004053 A1 * | 1/2002 | Biel | 424/277.1 |
| 2002/0091424 A1 * | 7/2002 | Biel | 607/88 |
| 2002/0165594 A1 * | 11/2002 | Biel | 607/89 |
| 2002/0173833 A1 * | 11/2002 | Korman et al. | 607/88 |
| 2002/0183808 A1 * | 12/2002 | Biel | 607/88 |
| 2003/0009205 A1 * | 1/2003 | Biel | 607/88 |
| 2003/0109906 A1 * | 6/2003 | Streeter | 607/88 |
| 2003/0216795 A1 * | 11/2003 | Harth et al. | 607/88 |
| 2005/0149150 A1 * | 7/2005 | McDaniel | 607/88 |

FOREIGN PATENT DOCUMENTS

| | | |
|---|---|---|
| WO | WO 97/04836 | 2/1997 |
| WO | WO 98/06456 | 2/1998 |

* cited by examiner

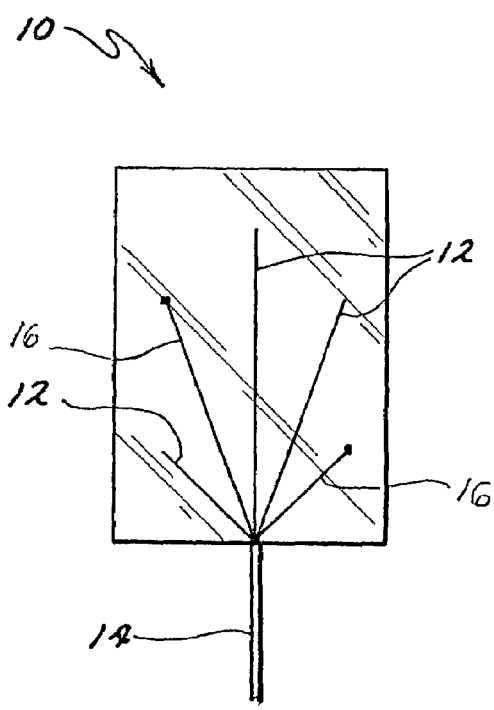
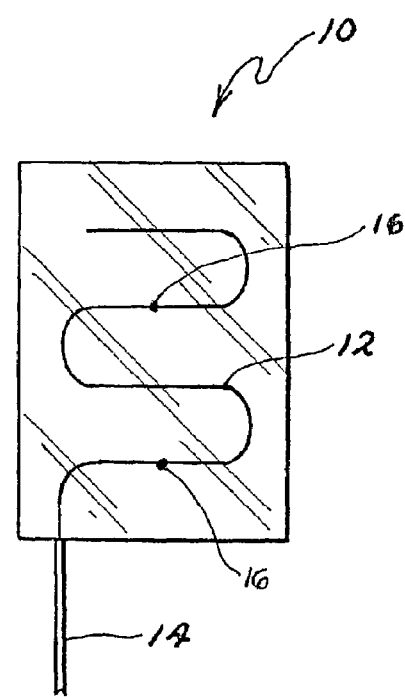
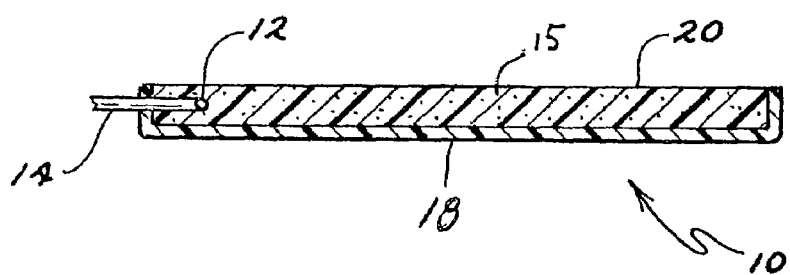

TREATMENT DEVICE FOR TOPICAL PHOTODYNAMIC THERAPY AND METHOD OF USING SAME

RELATED APPLICATIONS

This application is a continuation-in-part of U.S. application Ser. No. 09/513,036, which application claims the benefit of priority pursuant to 35 U.S.C. §120 of PCT application Serial No. PCT/US98/ 17589, filed Aug. 25, 1998.

BACKGROUND OF THE INVENTION

The invention relates to a medical device for photodynamic therapy (PDT). More specifically, the invention relates to a generally flexible or rigid conforming patch or pad and a shaped article such as a mouthpiece which provide light sources for topical PDT. The present invention advantageously uses light energy to treat or detect pathologies of living tissue, including cancer and microbiological pathogens. The present invention may be used in combination with photosensitizing agents.

SUMMARY OF THE INVENTION

The invention relates to a PDT treatment device which is configured to deliver light energy to a treatment site from a plurality of light emitting members disposed in the device. The treatment device may be flexible or rigid and used for wound treatment and biostimulation. The treatment device with light emitting members operates at wavelengths ranging from about 450 nm to about 850 nm; a dosage rate selected from within the range from about 0 to about 150 mw/cm$^2$; and a light dose ranging from 0 to about 300 J/cm$^2$. Dosage rates between about 25 mw/cm$^2$ to 150 mw/cm$^2$, about 50 mw/cm$^2$ to 150 mw/cm$^2$, and about 100 mw/cm$^2$ to 150 mw/cm$^2$ have been identified as particularly useful. Yet another useful dosage rate is approximately 150 mw/cm$^2$. The treatment device may have surface monitor capabilities which include isotropic or anisotropic light detectors or photodetectors. The light detectors may be used in combination with a controller to automatically monitor light dosage, light power and dosage rate.

In a preferred embodiment, a surface-conforming substrate such as a light diffusing gel element contains an integrated array of vertical cavity surface emitting lasers (VCSEL) as a light emitting source for topical PDT treatment.

In another embodiment, a shaped article is configured to direct energy and is used for PDT treatment. One embodiment of the shaped article includes a mouthpiece for covering and treating a patient's gumline. Another embodiment includes a shaped article for treatment of the roof of a mouth.

The invention relates to a light emitting treatment device including a light diffusing substrate and a plurality of light members. The light members are configured to emit energy from the assembly for photodynamic therapy of a body surface. The light diffusing substrate may be made of a polymeric material. The treatment device may include an adhesive element or layer for adhesively securing the device at a treatment field. The treatment device may be substantially flexible or substantially rigid and conform to a body surface. The light members may be disposed in a substantially uniform array. The light members may be configured to emit energy in a substantially uniform pattern. The light members may be configured in a light diffusing layer. The light emitting treatment device may further include a light reflective or blocking layer, such as a layer of gold or gold alloy. The light reflective or blocking layer may be selectively configured to control an area of illumination upon a treatment field. The light reflective or blocking layer may be a removable and disposable element. A kit may be provided containing a plurality of differently-sized light reflective or blocking elements for selected application on the light diffusive substrate. For example, a light blocking layer or element may be sized in relation to a given region upon the treatment field to substantially contain light illumination to the region.

The invention also relates to a light emitting device including a shaped member having one or more surfaces. The shaped member is configured to be disposed proximate one or more body surfaces. One or more light members are disposed in the shaped member and are configured to emit energy to the one or more body surfaces for photodynamic therapy. The light emitting device may further include a remote light source operatively coupled to the shaped member via at least one of a fiber optic element, a plurality of internally embedded filaments, or one or more VCSELs, LEDs, laser diodes, or other light emitting devices, or combinations thereof. The shaped member may include a silicone element having light diffusing characteristics. The shaped member may be configured to treat a gum line for a disease. The one or more light members may be embedded in the shaped member. The shaped member may further include a control operatively coupled to the shaped member to provide a range of intensity or selective operation of the emitted energy. The control may be used to operate the emitted energy in selected pattern or for selective periods of time.

The invention also relates to a method of using a light emitting treatment device including: identifying an area of treatment on a body surface; applying a surface of a light emitting treatment device to a body surface or tissue. Light members are configured to emit energy at a treatment site; activating a light transmitting source for a period of time such that the one or more light members emit energy at the area of treatment for photodynamic therapy. The method may further include injecting a drug through the treatment device into the body.

The treatment device may include one or more light detectors configured to provide surface monitoring. The light emitting treatment device may provide light wavelengths ranging from about 450 nm to about 850 nm; a light dosage rate ranging from about 0 mw/cm$^2$ to about 150 mw/cm$^2$; and a light dose ranging from 0 J/cm$^2$ to about 300 J/cm$^2$. Additional dosage rates of interest include the ranges from 25 to 150 mw/cm$^2$, 50 to 150 mw/cm$^2$, and 100 to 150 mw/cm$^2$. A particular dosage rate of interest is approximately 150 mw/cm$^2$.

Yet another object of the present invention is the provision of a heat dissipating element, member, or structure for removing heat generated by the one or more light members during operation. The heat dissipating element may include one or more heat sinks, fans, liquid cooling devices or combinations thereof. The heat dissipating element may be configured to transfer a substantial amount of the heat generated by the light members so that the surface or core temperature at a tissue field is not substantially raised during a photodynamic therapy of the present invention.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

BRIEF DESCRIPTION OF THE DRAWINGS

Preferred embodiments of the invention will be described in detail hereinafter with reference to the accompanying drawings, in which like reference numeral refer to like elements throughout, wherein:

FIG. 1 is a plan view of a light-emitting and light diffusing treatment device showing a plurality of radially diverging optical filaments;

FIG. 2 is a plan view of a light-emitting and light diffusing treatment device showing a serpentine optical filament;

FIG. 3 is a cross-section of a light-emitting and light diffusing treatment device;

DETAILED DESCRIPTION OF THE INVENTION

Figure 4:
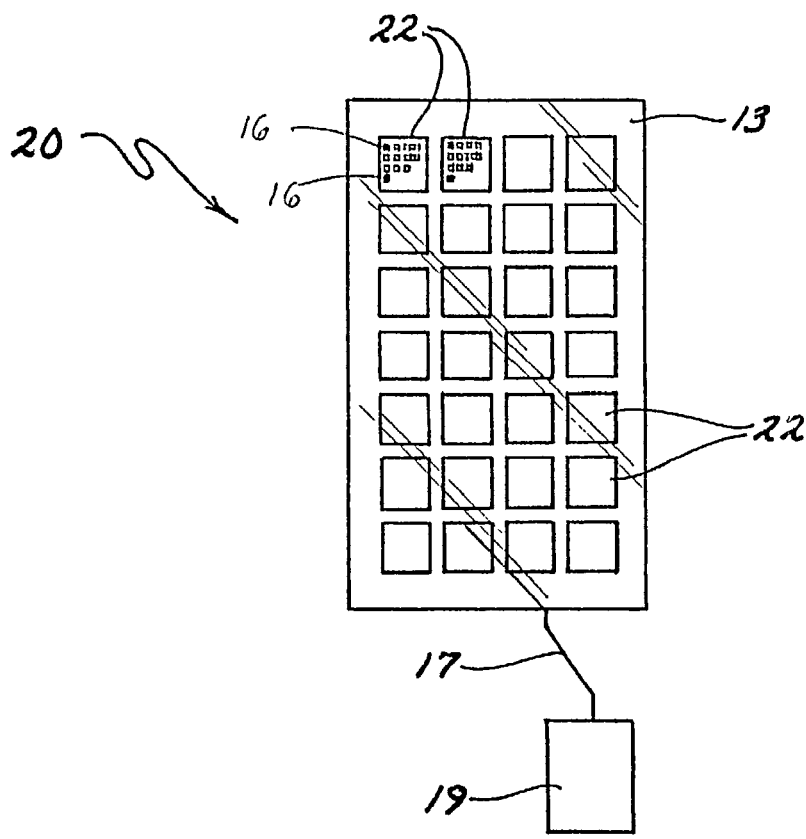
FIG. 4 is a plan view of a plurality of VCSELs arrayed in a treatment device coupled to an independent power supply.

In accordance with this invention, a treatment device 10, 20, 30, 40, 50 such as a patch, pad or shaped article is used to treat the surface tissue within a treatment field in a photodynamic therapy.

The present invention may be used in conjunction with or in relation to inventions disclosed in the following applications of the applicant, including:

Method of Enhancing Photodynamic Therapy by Administering an Immunologic Adjuvant, U.S. patent application Ser. No. 09/139,861, pending;

Expandable Treatment Device for Photodynamic Therapy and Method of Using Same, U.S. patent application Ser. No. 09/239,353, now U.S. Pat. No. 6,159,236;

Spatial Orientation and Light Sources and Method of Using Same for Medical Diagnosis and Photodynamic Therapy, U.S. patent application Ser. No. 09/139,862, now U.S. Pat. No. 6,048,359;

Dye Treatment Solution and Photodynamic Therapy and Method of Using Same, U.S. Pat. No. 6,251,127;

Method of Enhancing Photodynamic Therapy by Administering an Immunologic Adjuvant, Ser. No. 09/139,861;

Methylene Blue and Toluidene Blue Mediated Flourescence Diagnosis, U.S. Pat. No. 6,083,487;

Photodynamic Therapy Utilizing a Solution of Photosensitizing Compound and Surfactant, Ser. No. 09/514,070;

Photodynamic Cellular and Acellular Organism Eradication Utilizing a Photosensitive Material and Surfactant, Ser. No. 09/792,578;

Cellular or Acellular Organism Eradication via Photodynamic Activation of a Cellular or Acellular Organism Specific Immunological Response, Ser. No. 09/782,841;

Photodynamic Cellular and Acellular Organism Eradication Utilizing a Photosensitive Material and Benzalkonium Chloride, Ser. No. 10/026,198; and Apparatus and Method of Photodynamic Eradication of Organisms Utilizing Pyrrolnitrin, Ser. No. 10/052,990.

All information within these patents and applications is incorporated by reference herein in their entireties for all purposes.

Reference is made to FIGS. 1, 2 and 3, which illustrate a treatment device 10 having a plurality of optical filaments 12 and a plurality of light detecting elements 16. The treatment device 10 is used to treat an area of skin or exposed (or exposable) tissue with topical or surface exposure of PDT including generally uniform intensity light energy for long periods. FIG. 2 illustrates another embodiment of a treatment device 10 having a serpentine optical filament 12.

FIG. 3 illustrates a cross-section of a treatment device 10. Treatment device includes a flexible substrate element 15 which may be of a light diffusive material, such a silicone. The treatment device 10 has an exposed surface 20 on the treatment field-facing side. One or more optical or light-transmitting filaments 12 may be imbedded in substrate 15. The silicone material of element 15 may generally diffuse the light transmitted from the filaments 12 uniformly over an area of the body being treated. A light-blocking or reflective element 18, such as gold or other metallic layer, may be disposed upon one or more surfaces of the treatment device. Element 18 may be a reflective plastic film. Additional light-blocking or reflective elements may be provided upon substrate element 15 between light members 12 and the treatment field, such as disclosed in FIG. 7.

One or more optical filaments 12 may be incorporated in the treatment device 10. The filaments 12 may be formed integral with or operatively connected to an optical fiber 14 and coupled with a remote light source (not shown). The filaments 12 are disposed in a suitable array which uniformly and efficiently disperses the light energy throughout the operative area of the treatment device 10. The array pattern may include radiating spokes or a serpentine configurations as shown in FIGS. 1–2 or other variations and combinations thereof.

The treatment device 10 advantageously conforms and, if necessary, stretches slightly to contact and cover a desired area for PDT. The treatment device 10 uniformly distributes light energy within the area being treated. The treatment device 10 is generally easily removed from the skin or tissue of the patient without discomfort or adverse affects on the tissue. A hypodermic syringe may be used to inject a therapeutic agent or marker through the treatment device 10 without removal or lifting during treatment. Treatment device 10 may be adhesively secured at a treatment field during a photodynamic therapy. An adhesive layer may be provided on a surface of treatment device 10, or a separate adhesive device (not shown) may be used to secure treatment device 10 at the treatment field.

A treatment device of the present invention may include a plurality of discrete light emitting elements disposed within a flexible substrate 15. FIG. 4 illustrates one particular embodiment of the present invention. FIG. 4 illustrates a plurality of array tiles 22 made of VCSELs arrayed in a treatment device 20 which is coupled to an independent power supply 19. A plurality of array tiles 22 made of VCSELs, light emitting diodes (LEDs), laser diodes, or other light emitting elements are disposed in an array or pattern and adhered to or mounted within a substrate 13 to form a treatment device 20. The treatment device 20 is operatively coupled to an adjustable, self-contained power source 19 such as battery using a conventional wire 17 or cable. The array tiles 22 comprising VCSELs, LEDs, laser diodes, or other light emitting elements may be wired in series, parallel, or combinations of series and parallel using suitable patterns among adjacent rows or via a peripheral scheme.

The treatment devices 10, 20, 30, 40 may have one or more surface monitor members 16 such as isotropic or anisotropic light detectors or photodetectors. The surface monitor members 16 may be used in combination with a controller 60 to automatically monitor and control characteristics such as light wavelength (nm), light dosage (joules/cm$^2$), and light dosage rate (mw/cm$^2$).

Figure 5:
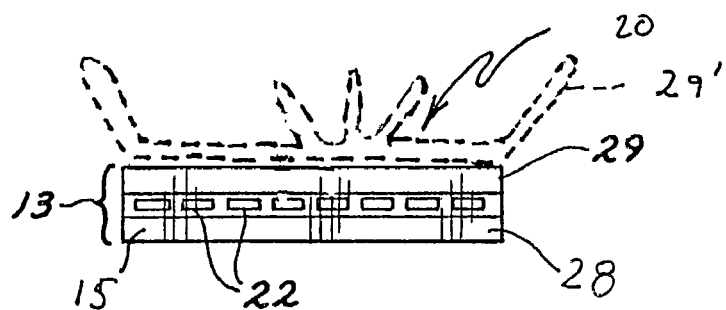
FIG. 5 is a side elevation view of the layers of the treatment device of FIG. 4 with an intermediate layer of VCSELs disposed between a heat dissipating layer and a light diffusing layer.

FIG. 5 illustrates a cross-sectional view of an embodiment of a treatment device 20 with an intermediate layer of array tiles made of VCSELs 22 or other light emitting elements disposed between a heat dissipating element 29 and a light diffusing layer 28. The light diffusing layer 28 is preferably made of a silicone rubber material, and the heat-dissipating element 29 is preferably made of a material configured to absorb or disperse heat generated by the plurality of light emitting elements 22. Heat dissipating element 29 may be configured to transfer heat generated by light members 22 away from the treatment field so that the local or core temperature of the treatment field is not substantially increased during a photodynamic therapy. The heat dissipating element may be a heat sink indicated as 29' (shown in phantom lines in FIG. 5), such as a finned heat radiator common in the electronics industry. Heat dissipating element 28 may be a fluid-filled heat sink. Another heat dissipating element 29 may include a fan device (not shown) for forcing air to cool treatment device 20. Yet another heat dissipating element 29 may include a fluid system which utilizes a cooling fluid to transfer heat generated by the light sources 22 away from the treatment field. A fluid-based system may include a pump (not shown) for circulating fluid relative to treatment device 20. Those skilled in the relevant arts would appreciate that alternative methods or materials may be used for heat dispersion.

Light emitting members 22 may be disposed in close proximity to one another, or spaced apart to facilitate flexing of the substrate 13. An embodiment of the substrate 13 preferably has dimensions of about 3.0 cm by 1.2 cm and includes 0.3 cm×0.3 cm array tiles made of VCSELs. Light detectors 16 may be disposed integrated within the array of VSCEL's 22, or be separately configured.

The particular pattern or configuration of light sources 22 within the treatment device 20, 30, 40 may be determined by routine experimentation. For example, the number of VCSELs 22 per array may be selectively determined and will vary depending upon factors including the required light output (in mw/cm$^2$). The light sources, such as VCSELs, are separated or spaced-apart from the tissue surface by a predetermined distance that is dependent upon factors including the incident light energy necessary for treatment, beam divergence, and the thickness or opacity of the light diffusing layer 28. The separation may be approximately 1–2 mm. The array may be sufficiently flexible or malleable to conform to a variety of body shapes or parts such as the tongue, palate, or cheek, as well as normally exposed skin areas having complex or irregular curvatures or tight curves, such as a patient's arm or leg, finger or toe, heel, wrist, elbow.

An alternative to VCSEL light sources 22 would include one or more LEDs, laser diodes, or other light emitting elements. For a methylene blue-based photodynamic therapy the LEDs may be selected to radiate light at approximately 665±7 mn.

Treatment devices 10, 20, 30, 40 of the present invention may be utilized in a photodynamic therapy utilizing a known photosensitive material. Photosensitive materials which may find applicability in practicing the present invention include, but are not limited to, the following:

| PHOTOSENSITIVE MATERIAL | WAVELENGTH |
|---|---|
| Hypiricin | 550–660 nm |
| Aluminum phthalocyanine | 670–675 nm |
| Merocyanine | 500–560 nm |
| Psoralen | 320–400 nm |
| Rose Bengal | 548 nm |
| Acridine orange | 489 nm |
| Indocyanine green | 660 nm |
| Nile blue | 628 nm |
| Nile red | 553 nm |
| Toluidine blue | 560–660 nm |
| Methylene green | 600–670 nm |
| Lutetium Texaphyrin | 732 nm |
| Benzporphyrin derivative | 690 nm |
| Foscan (mTHPC) | 652 nm |
| Tin ethyl etiopurpurin | 664 nm |
| Photofrin (porfimer solution) | 630 nm |
| Aminolevulinic Acid | 630 nm |

Figure 6:
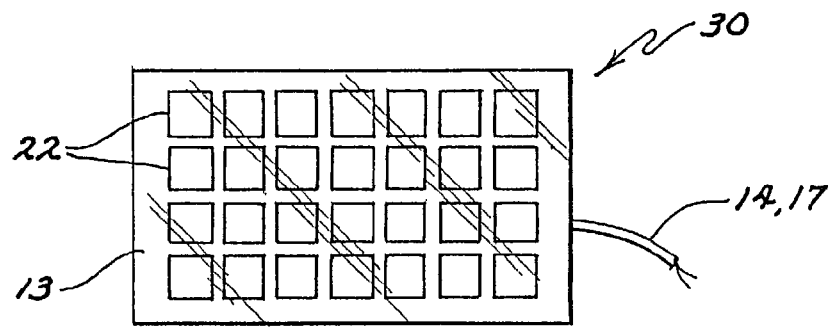
FIG. 6 is a plan view of a treatment device having VCSELs.

FIG. 6 illustrates a treatment device 30 having a plurality of array tiles 22 made of VCSELs.

Figure 7:
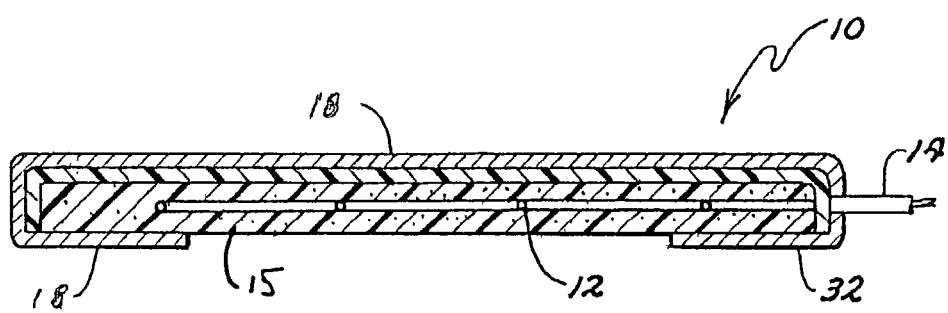
FIG. 7 is a cross-sectional view of an embodiment of the light emitting treatment device.

FIG. 7 illustrates an embodiment of the treatment device 10 with a layer 18 of material such as gold is disposed on one or more surfaces to contain the PDT to a certain area. The layer 18 may be added at the time of treatment depending on the treatment area desired. Additionally, the reflective layer 18 may be configured in relation to the size of the treatment field.

Figure 8:
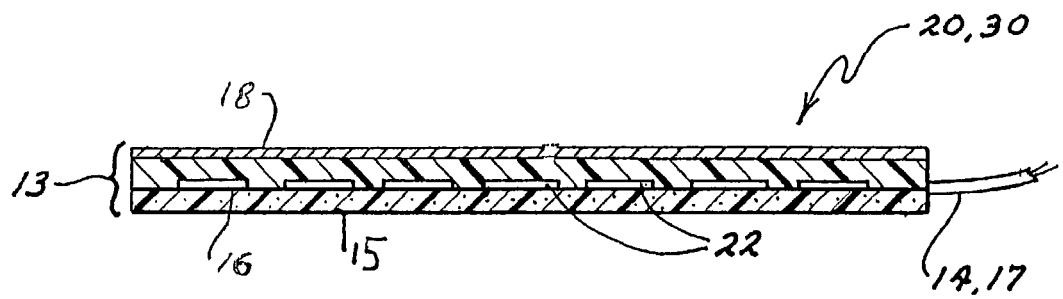
FIG. 8 is a cross-sectional view of another embodiment of the light emitting treatment device of FIG. 6.
Figure 9:
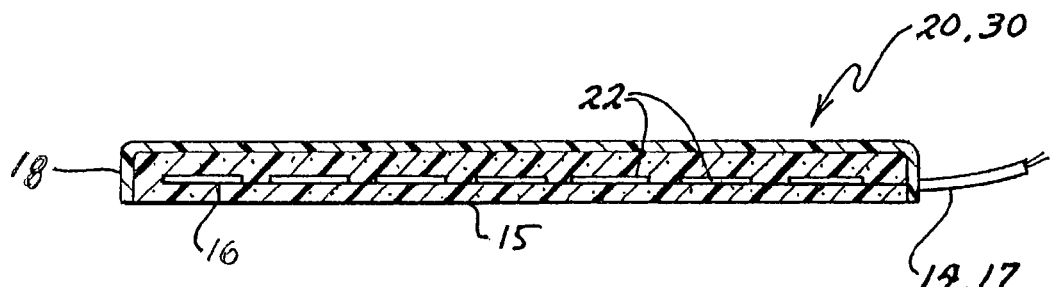
FIG. 9 is a cross-sectional view of another embodiment of the light emitting treatment device of FIG. 6.

FIGS. 8 and 9 illustrate other embodiments of the treatment device 20, 30 of FIGS. 4 and 6.

Figure 10:
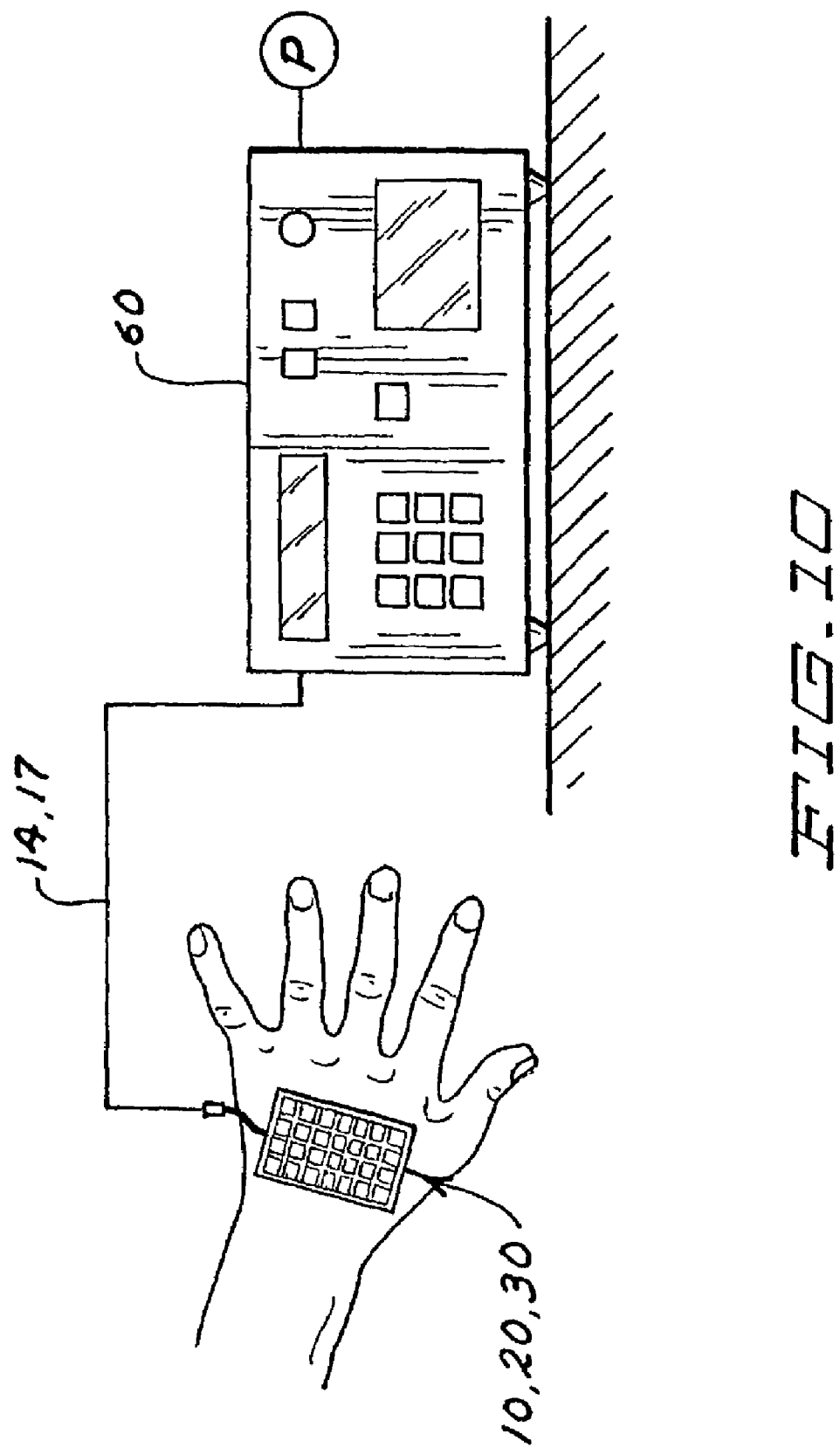
FIG. 10 is a view of the light emitting treatment device disposed on a body surface along with an associated energy source.

FIG. 10 illustrates a treatment device 10, 20, 30 disposed on a body surface along with an associated energy source and controller 60. The controller 60 may receive feedback from the treatment device 10 to operatively control treatment variables, such as light dosage, light intensity, etc. Light intensity feedback may be via light detector elements 16 of the treatment device 10.

Figure 11:
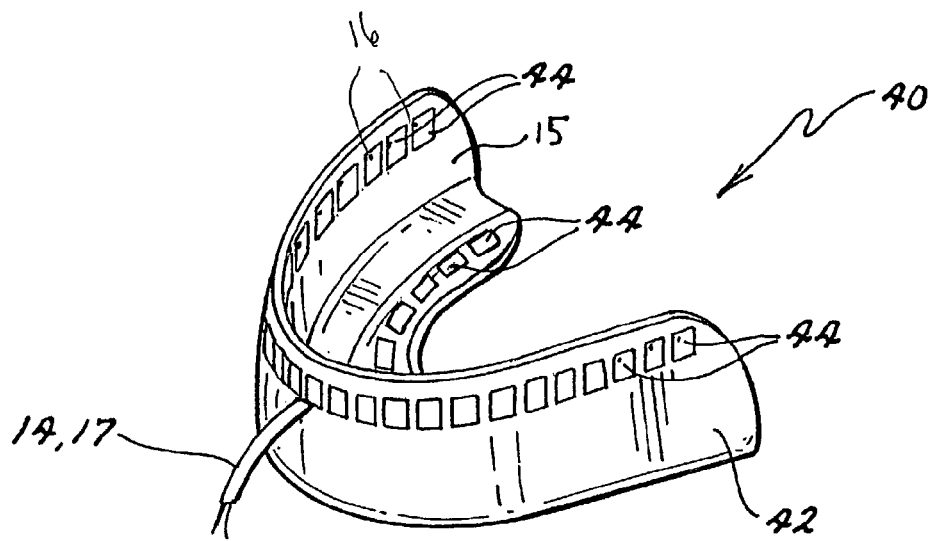
FIG. 11 is a shaped device shaped in the form of a mouth piece having energy emitting members.
Figure 12:
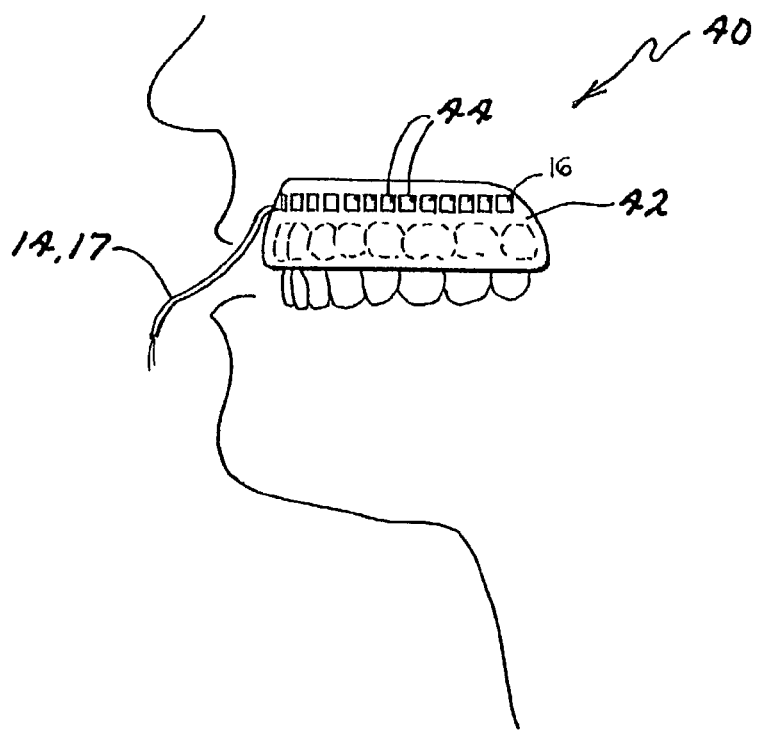
FIG. 12 is a side view of the shaped device of FIG. 11 disposed in a mouth of a patient for PDT.

FIG. 11 is a shaped device 40 that is shaped in the form of a mouthpiece 42 and includes energy emitting members 44. One embodiment of the shaped device 40 is in the form a mouthpiece which may be applied over the teeth and gums of a patient for the treatment of cancer or for tissue sterilization. The shaped device 40 may be formed of silicone rubber or a similar light diffusing material that will conform to a surface area to be treated using PDT. The shaped device 40 is operatively coupled to a remote light source using a fiber optic element or a plurality of internally embedded filaments. Alternatively, the shaped device may itself contain one or more VCSELs, LEDs, laser diodes, or other light emitting devices disposed in a array tile or pattern and is operatively coupled to a remote power supply. FIG. 12 illustrates the shaped device 40 disposed in a mouth of a patient. Treatment device 40 may include light intensity sensors 16 to provide feedback to the controller 60 during a PDT treatment.

Figure 13:
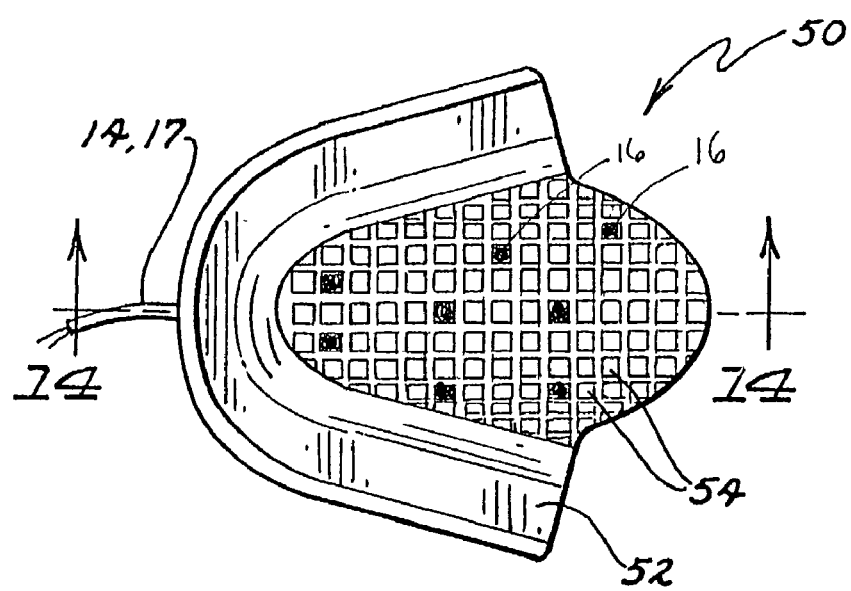
FIG. 13 is another embodiment of the shaped device.
Figure 14:
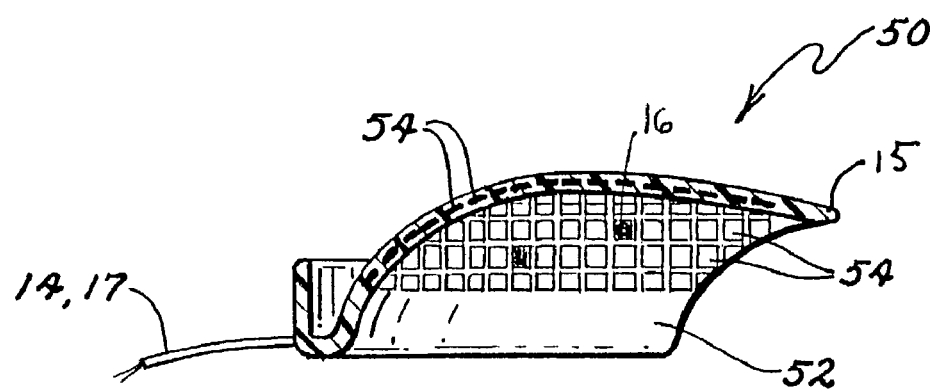
FIG. 14 is side view of the shaped device of FIG. 13 taken along the line of 14—14.

FIG. 13 illustrates another embodiment of the shaped device 50 that is in the form a mouthpiece 52. The mouthpiece 52 includes energy emitting members 54 that are used for PDT of the roof of the mouth. FIG. 14 illustrates the mouthpiece 50 of FIG. 13 taken along the line of 14—14. Treatment device 50 may include light intensity sensors 16 to provide feedback to the controller 60 during a PDT treatment.

Treatment device 10, 20, 30, 40, 50 may include one or more light sources to provide illumination at the tissue field. The one or more light sources may provide light wavelengths ranging from about 450 nm to about 850 nm. The one or more light sources may include VCSELs, LEDs, laser diodes, other light emitting devices, or a combination thereof. A particular light source may be selected with reference to a particular photosensitive material to be utilized in a photodynamic therapy. The light source may provide a light dosage rate ranging from about 25 mw/cm$^2$ to about 150 mw/cm$^2$; and a light dose ranging from 0 J/cm$^2$ to about 300 J/cm$^2$. Additional dosage rates of particular interest include the range from about 25 to about 150 mw/cm$^2$, about 50 to about 150 mw/cm$^2$, and about 100 to about 150 mw/cm$^2$. Another particular dosage rate of interest is approximately 150 mw/cm$^2$.

Treatment device 10, 20, 30, 40, 50 may include two or more different light emitting elements selected to emit light at two or more different light ranges. Each of the two or more different light emitting elements may be separately controlled for simultaneous or individual operation. For example, first and second different light sources may be utilized in consecutive or alternative manners. Alternatively, two or more different light sources may be utilized simultaneously during a photodynamic therapy. Light sensitive materials may be selected for use with reference to the two or more different light sources. The two or more different light sources may provide two or more different light bands. For example, a narrow band light source may be used in combination with a broad band light source. The two or more different light emitting elements may be selectively configured and controlled to provide appropriate wavelengths and dosage rates to the treatment field.

Treatment device 10, 20, 30, 40, 50 may be adhesively secured at a treatment field during a photodynamic therapy. An adhesive layer may be provided on a surface of treatment device 10, or separate adhesive devices (not shown) may be used to secure treatment device 10 at the treatment field. A variety of adhesive techniques may be appropriate as appreciated by those skilled in the relevant arts.

Treatment device 10, 20, 30, 40, 50 may include one or more light blocking or light reflective layers or element 18 for controlling the extent of light source illumination. Element 18 may be a metallic layer, such as gold. Element 18 may be a plastic having a reflective layer. Element 18 may be selectively configurable at the time of use, such as by trimming or shaping element 18. Element 18 may be selectively configured in relation to the size of the treatment field. Element 18 may be provided in a kit of a plurality of differently sized or configured elements. Element 18 may be a disposable part removable from treatment device 10, 20, 30, 40, 50 after a photodynamic therapy. An adhesive layer may be provided on one or more surfaces of element 18 to facilitate attachment between element 18 and the treatment field, attachment between element 18 and device 10, 20, 30, 40, 50, or both.

A method of using treatment device 10, 20, 30, 40, 50 in a photodynamic therapy may include the steps of: (1) providing a photosensitive material to a treatment field, (2) activating a treatment device in association with the treatment field so that at least a portion of the treatment field is illuminated with light emitted from the treatment device, and (3) waiting a period of time during which the photosensitive material is photodynamically activated. The photosensitive material can be administered to a treatment field via one or more of a variety of known delivery approaches, including but not limited to inhalation, injection, ingestion, topical application, etc. The photosensitive material can be provided to the treatment field after the treatment device has been placed at the treatment field. For example, the photosensitive material can be delivered via an injection passing through the treatment device. The treatment device can be placed in touching relationship to the treatment field or may be suspending a distance away from the treatment field. The period of time of a photodynamic therapy may be a period of minutes or a period of hours. Additional steps may include: providing a light blocking or reflective element to selectively control an area of illumination on the treatment field, and providing a heat dissipating element in relation to the treatment device to remove heat generated by the device so that the treatment field temperature is not substantially increased during the photodynamic therapy.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

The invention claimed is:

1. A method of performing a photodynamic therapy at a treatment field, said method comprising the steps of:

providing a photosensitive material to the treatment field;

providing a flexible polymer patch element having a treatment surface and an opposite surface displaced a patch thickness away from the treatment surface, said patch element having a light block layer on the treatment surface and a light reflective layer on the opposite surface;

emitting light from a plurality of light emitting members disposed within the patch element between the light blocking layer and the light reflective layer with at least a portion of the patch element being between the plurality of light emitting members and the light block layer and at least another portion of the patch element being between the plurality of light emitting members and the light reflective layer;

applying the patch element at the treatment field, said treatment surface conforming to a surface of a tissue field;

directly passing at least some of the emitted light to the treatment field through a thickness of the flexible polymer patch which is substantially less than a local thickness of the patch element;

reflecting at least some of the emitted light off the light reflective layer and back towards the treatment surface, said reflected light passing through an effective thickness of the flexible polymer patch which is substantially greater than the local thickness of the patch element and as a result said reflected light being more diffused relative to the light passing directly to the treatment surface; and blocking at least some of the emitted light with the light blocking layer, together the passed light and the reflected light providing a light dosage rate to the treatment field of between 0 mw/cm$^2$ to about 150 mw/cm$^2$.

2. The method of claim 1 wherein the step of providing the photosensitive material to the treatment field is achieved through one or more of the following administration approaches: topical application, injection, inhalation, and ingestion.

3. The method of claim 1 wherein the plurality of light emitting members provide a light dosage rate to the treatment field at a value between about 50 mw/cm$^2$ to about 150 mw/cm$^2$.

4. The method of claim 1 wherein the plurality of light emitting members provide a light dosage rate to the treatment field at a value of about 100 mw/cm$^2$ to about 150 mw/cm$^2$.

5. The method of claim 1 wherein the plurality of light emitting members provide a light dosage rate to the treatment field at a value of about 150 mw/cm$^2$.

6. The method of claim 1 further comprising the steps of: dissipating heat away from the plurality of light members and away from the treatment field with a heat dissipating element.

7. The method of claim 1 wherein the light blocking layer is selectively configured in relation to an area within the treatment field.

8. The method of claim 7 wherein the light blocking layer is provided from a kit containing a plurality of differently configured light blocking elements.

9. A method for photodynamic treatment at a treatment site, said method comprising the steps of:

providing a photosensitive material to a treatment field;

positioning a patch element upon a surface of the treatment field, said patch element having a body and being of a flexible polymer so as to conform to the surface of the treatment field, said patch element having a treatment surface in contact with the treatment field and an opposite surface, said patch element having a light reflective layer proximate the opposite surface and a light blocking layer proximate to the treatment field;

illuminating a light member within the body of the patch element;

passing some of light from the light member directly to the treatment field;

reflecting some of the light from the light member off the reflective layer and back to the treatment field; and blocking some of the light from the light member from passing directly into the treatment field, wherein the light member provides a light dosage rate to the treatment field of between 0 mw/cm$^2$ to 150 mw/cm$^2$.

10. The method of claim 9 wherein the step of providing the photosensitive material to the treatment field is achieved through one or more of the following administration approaches: topical application, injection, inhalation, and ingestion.

11. The method of claim 9 further comprising the step of:

dissipating heat generated by the light member with a heat dissipating element connected to the substrate element.

12. The method of claim 9 wherein the light blocking layer has an aperture which is selectively configured in relation to an area within the treatment field.

13. The method of claim 9 wherein the light blocking layer is provided from a kit containing a plurality of differently configured light blocking elements.

14. The method of claim 9 wherein the step of providing the photosensitive material to the treatment field includes an injection passing through the patch element.

15. The method of claim 9 wherein the step of positioning the patch element upon the surface of the treatment field includes adhesively securing the patch element to the surface.

16. The method of claim 9 wherein the light dosage rate is between 100 mw/cm$^2$ to 150 mw/cm$^2$.

* * * * *